(12) United States Patent
Frampton

(10) Patent No.: US 8,602,646 B2
(45) Date of Patent: *Dec. 10, 2013

(54) DENTAL SENSOR HOLDER AND METHOD OF HOLDING A DENTAL SENSOR

(71) Applicant: ProEdge Dental Products, Inc., Centennial, CO (US)

(72) Inventor: Mark Frampton, Parker, CO (US)

(73) Assignee: ProEdge Dental Products, Inc., Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,027

(22) Filed: Jul. 2, 2013

(65) Prior Publication Data

US 2013/0294586 A1    Nov. 7, 2013

Related U.S. Application Data

(63) Continuation of application No. 13/575,862, filed as application No. PCT/US2011/026205 on Feb. 25, 2011, now Pat. No. 8,500,328.

(60) Provisional application No. 61/308,173, filed on Feb. 25, 2010.

(51) Int. Cl.
*A61B 6/14* (2006.01)

(52) U.S. Cl.
USPC .......................................... 378/170; 378/168

(58) Field of Classification Search
USPC ................................................... 378/168, 170
See application file for complete search history.

(56) References Cited

U.S. PATENT DOCUMENTS

| | | | |
|---|---|---|---|
| 1,536,341 A | 5/1925 | Hodgson | |
| 2,274,808 A * | 3/1942 | Rinn | 378/168 |
| 3,510,652 A * | 5/1970 | Greene et al. | 378/168 |
| 5,274,691 A * | 12/1993 | Neri | 378/183 |
| 6,461,038 B2 * | 10/2002 | Pellegrini et al. | 378/191 |
| 8,500,328 B2 * | 8/2013 | Frampton | 378/170 |
| 2007/0280424 A1 | 12/2007 | Schmulenson et al. | |
| 2009/0262802 A1 * | 10/2009 | Chujoh et al. | 375/240.08 |

OTHER PUBLICATIONS

EP Extended Search Report for EP Application No. 11748128.3, mailed Jul. 3, 2013.

* cited by examiner

*Primary Examiner* — Alexander H Taningco
(74) *Attorney, Agent, or Firm* — Swanson & Bratschun, LLC

(57) ABSTRACT

A dental sensor holder including a strip of pliable, longitudinally elastic material having two ends. The holder is constructed by permanently bonding the two ends of the strip to form a somewhat elastic loop. In addition, the sensor holder includes an adjustable bond portion on the inside of the loop which may selectively be engaged to join adjacent portions of the strip into a functional bitewing.

18 Claims, 2 Drawing Sheets

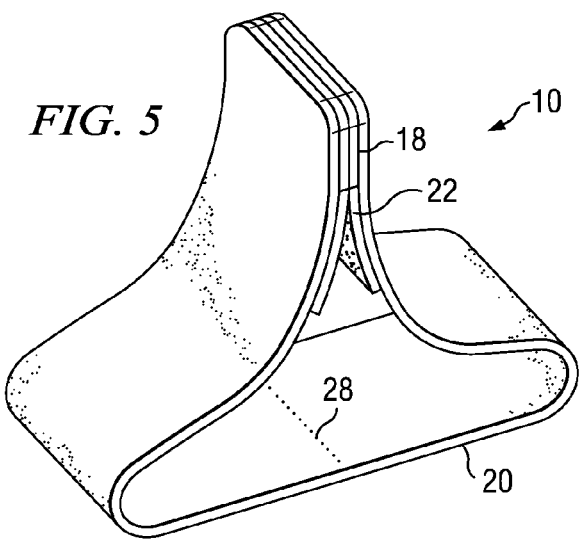
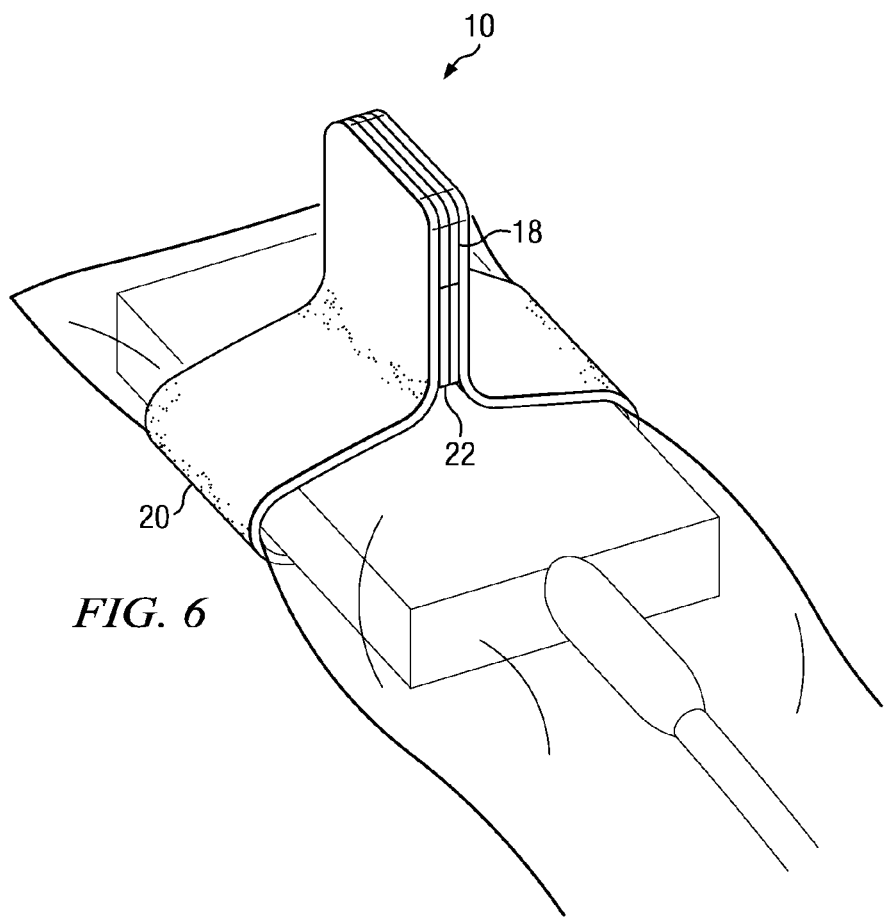

DENTAL SENSOR HOLDER AND METHOD OF HOLDING A DENTAL SENSOR

RELATED APPLICATIONS

This application is a continuation of U.S. patent application Ser. No. 13/575,862, filed on Jul. 27, 2012, entitled "Dental Sensor Holder and Method of Holding a Dental Sensor", which application is a 35 U.S.C. §371 national phase application of PCT/US2011/026205 (WO 2011/106620), filed on Feb. 25, 2011, entitled "Dental Sensor Holder and Method of Holding a Dental Sensor", which application claims the benefit of U.S. Provisional Application Ser. No. 61/308,173, filed Feb. 25, 2010, which is incorporated herein by reference in its entirety.

BACKGROUND

In the dental arts the term "bitewing" has two related meanings. In one instance a bitewing refers to a dental x-ray image or film designed to show the crowns of the upper and lower teeth simultaneously. Additionally, a bitewing may be defined as the holder for an x-ray film or sensor that includes a projecting fin on one side that in use is held between the teeth. According to this second definition, the bitewing, or bitewing holder, thus extends perpendicular to the plane of an x-ray film or sensor such that a dental patient may bite down on the bitewing while the film or sensor is inside of his or her mouth, opposite the x-ray source.

Historically, bitewings or bitewing tabs were simple cardboard devices which were attached to an x-ray film holder, used once and then thrown away. Many dentists no longer use x-ray film. On the contrary, x-ray images are often now acquired with digital electronic x-ray sensors.

Unlike a traditional x-ray film, a digital x-ray sensor (referred to herein as a sensor) is a reusable device. Typical sensors are provided in a substantially flattened package with a data cable extending from one end. In use the sensor will typically be associated with a bitewing type device to take bitewing images. Thus, in use a modern sensor is positioned in the same manner as a traditional film for a bitewing image, with the patient biting down on a projecting fin attached to the sensor.

Unlike conventional x-ray film, a sensor must be used multiple times. Therefore, sensors are typically placed within sterile disposable sheaths before use to avoid the transfer of germs or other substances from one patient to another. Various bitewing type holders have been developed which tightly wrap around the sensor or sensor sheaths or alternatively are bonded with adhesives to a sensor and sheath and which further provide a bitewing fin. Known sensor holders can be somewhat problematic to use because they can be uncomfortable for the patient, or difficult to install and remove from the sensor. For example, sensors may be easily damaged by pulling on the data cable during sheath or holder removal. A conventional holder applied loosely to facilitate removal may not adequately secure the sensor during the x-ray imaging process.

The embodiments disclosed herein are directed toward overcoming one or more of the above problems set forth above.

SUMMARY OF THE EMBODIMENTS

One embodiment is a dental sensor holder including or fabricated with a strip of pliable, longitudinally elastic material having two ends. The holder is constructed by permanently bonding the two ends of the strip to form a somewhat elastic loop. In addition, the sensor holder includes an adjustable bond portion on the inside of the loop which may selectively be engaged to join adjacent portions of the strip into a functional bitewing.

The dental sensor holder may also include a fold line transverse the width of the strip at a point corresponding to the midpoint of the loop opposite the permanent bond. The adjustable bond may be a "hook and hook" or a "hook and loop" type adjustable fastener. For example, the adjustable bond may include a first attachment surface associated with a strip at an inner surface of the loop near the permanent bond and a second attachment surface associated with the inner surface of the looped strip on the opposite side of the permanent bond from the first attachment surface.

The length of the strip between the first and second attachment surfaces away from the permanent bond will typically be selected to be less than the circumference of a desired dental imaging sensor. Accordingly, in use, the sensor and a sheath may be placed loosely into the loop over the central fold line and away from the permanent bond. Then, the adjustable bond may be engaged by pressing the first and second attachment surfaces together thereby accomplishing two tasks: first, the first and second attachment surface and the portion of the looped strip associated with the first and second attachment surfaces will engage to form a bitewing tab. Second, the portion of the loop opposite the bitewing tab will properly and generally securely support the sensor for use taking a bitewing image. Since the strip used to form the loop is slightly elastic in the longitudinal direction and typically slightly less in length than the circumference of the selected sensor, the loop opposite the bitewing tab will gently, but firmly support the sensor.

Selective articulation of the adjustable bond may be used to accommodate reasonable variations in the size of a sensor. For example, the user may engage all or only a portion of the first and second attachment surfaces which allows a user to accommodate sensors having different circumferences. In addition, the adjustable bond allows the user to easily open the loop after use for the safe and convenient removal of the sensor or sheath.

An alternative embodiment disclosed herein is a method of fabricating a dental sensor holder as described above. Another alternative embodiment is a method of holding a dental sensor for a bitewing image, using a dental sensor holder as described above.

BRIEF DESCRIPTION OF THE DRAWINGS

FIG. 5 is a perspective view of a dental sensor holder with an adjustable bond unattached.

FIG. 6 is a perspective view of a dental sensor holder in use with the adjustable bond attached.

DETAILED DESCRIPTION

Figure 1:
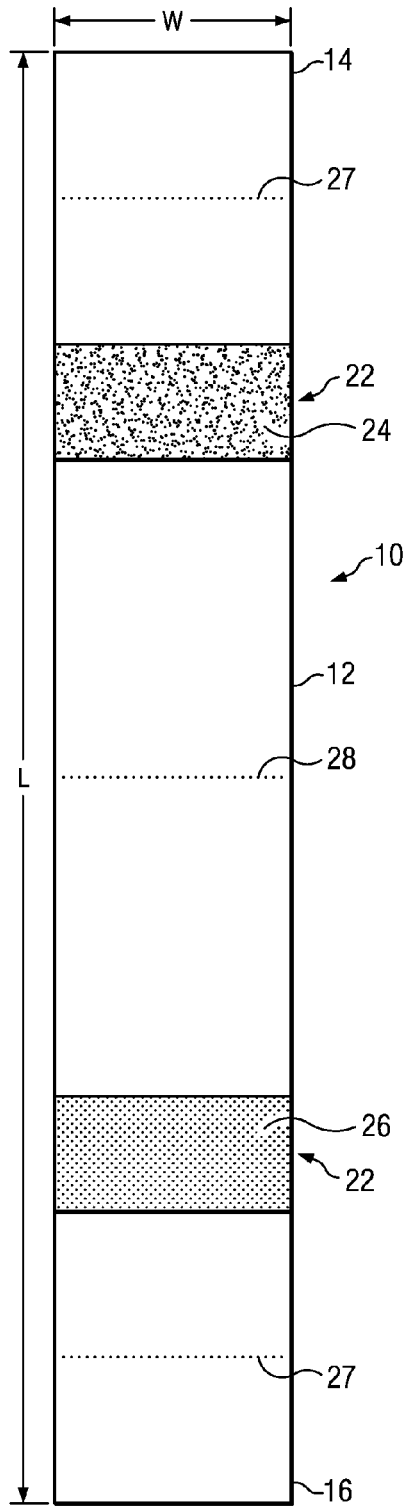
FIG. 1 is a plan view of a disclosed dental sensor holder prior to the formation of the dental sensor holder into a loop.

One embodiment is a dental sensor holder 10 as shown in FIGS. 1-6. FIG. 1 is a plan view of the dental sensor holder 10 before the dental sensor holder 10 is formed into a loop and before a permanent bond is made or trimming occurs as described below. The dental sensor holder 10 includes a strip 12 of a pliable longitudinally elastic material. The strip 12 may be fabricated from any material which is pliable and longitudinally elastic. The most suitable materials will however be substantially water resistant, soft and inherently clean since the dental sensor holder 10 will be placed within a dental patient's mouth. 30 mm thick polyethylene foam has been determined to be a well suited material for the strip element. Other functionally similar foams, plastics, or similar materials would be suitable for the fabrication of the strip element as well.

Figure 2:
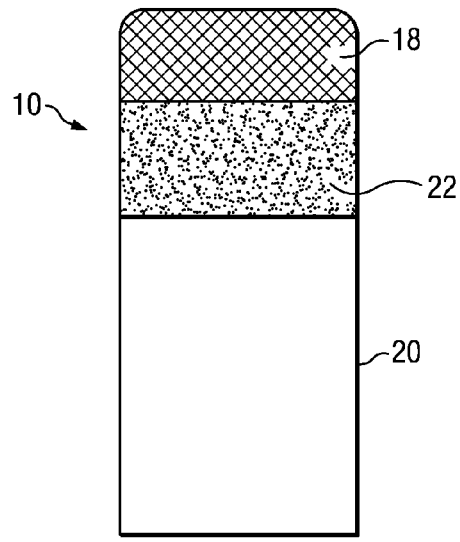
FIG. 2 is a front elevation view of the dental sensor holder of FIG. 1, after the holder has been formed into a loop and trimmed.
Figures 3, 4:
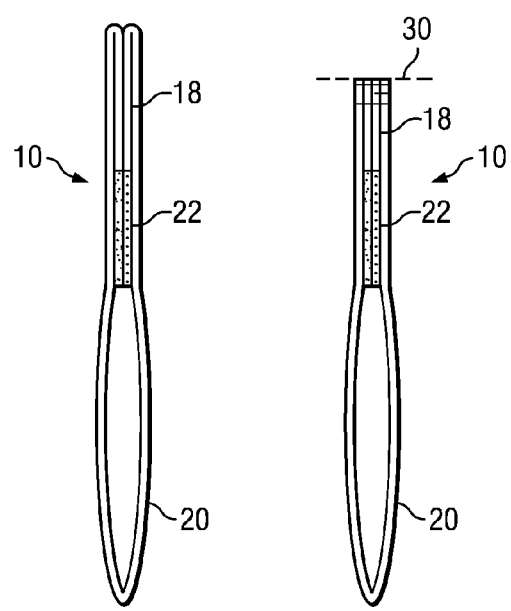
FIG. 3 is a side elevation view of a dental sensor holder after the holder has been formed into a loop but before the dental sensor holder is trimmed.
FIG. 4 is a side elevation view of a dental sensor holder after the holder has been formed into a loop and trimmed.

As also shown in FIG. 1, the strip 12 has a length L and a width W and two ends 14 and 16 respectively. The two ends 14 and 16 will be joined in a permanent bond 18 as shown in FIGS. 2-4 as a manufacturing step prior to delivery of the dental sensor holder 10 to a dentist for use. Connection of the two ends 16 and 14 with a permanent bond causes the strip 12 to form a loop 20. The permanent bond may be made with an adhesive, a heat generated weld or any other bonding process that is suitable for bonding the strip material.

Referring back to FIG. 1, the dental sensor holder 10 also includes an adjustable bond 22 which provides for the selective and adjustable joining or connection of selected portions of the strip extending on each side of the strip 12 from the region of the permanent bond 18 toward opposite, open, portions of the loop. In the embodiment depicted in FIG. 1 the adjustable bond includes a first attachment surface 24 and a second attachment surface 26 which may selectively be attached or bonded together and then separated.

The first and second attachment surfaces 22, 24 may be fabricated of any suitable material; however, hook and loop fasteners or hook and hook or similar fasteners may be utilized to implement the adjustable bond. Any material which is well suited for the first or second attachment surface will be easily joined together and easily separated while maintaining a stable connection or bond prior to separation. Ideally the adjustable bond will be of similar thickness when compared to known bitewing tabs, comfortable in the mouth and resistant to shear stress. The ULTRA-MATE® PS731 Product of the Velcro® companies is particularly well suited for the implementation of the first and second attachment surfaces. ULTRA-MATE® PS731 and similar fasteners which may be developed in the future includes scale-like extrusions which interlock and grip one another and have substantially greater shear strength than conventional hook and loop fasteners.

It may be advantageous to form the permanent bond 18 with multiple thickness of the strip material bonded together. For example, as shown in FIG. 1 and the side view of FIGS. 3-4 each end of the strip, 14 and 16 may be folded over along a perforated fold line 27 and bonded together at each adjacent surface to fabricate a permanent bond having a total of four thicknesses of strip material. In use, multiple thicknesses of the strip material at the location of the permanent bond provides for a consistent overall bitewing tab thickness along with the adjacent adjustable bond structure when the adjustable bond is engaged.

It may also be noted that the permanent bond greatly facilitates the accurate but quick and easy alignment of the first and second attachment surfaces 24 and 26 respectively. It is important that the attachment surfaces 24, 26 be accurately aligned such that all portions of the attachment surface are covered by the relatively soft strip material in use. Thus, accurate alignment helps avoid irritation of a patient's mouth tissue by the first and second attachment surfaces or other adjustable bond structure in use.

The dental sensor holder 10 may include an optional perforated fold line 28 at the midpoint of the strip as shown in FIG. 1. This fold line assists in the fabrication of a loop from the strip and further defines the center point of the sensor receiving portion of the loop.

The looped over strip portions of the dental sensor holder dental at the top of the permanent bond as shown in FIG. 3 may be trimmed along a trim line 30 as shown in FIG. 4. Typically, any trimming step will be part of the manufacturing process, performed after the permanent bond is created but before the dental sensor holder is delivered to a dentist for use. In addition, the top edges of the permanent bond region may be rounded as shown in FIG. 2 and FIGS. 5-6 to enhance patient comfort through the elimination of potentially irritating corners.

The dental sensor holder 10 is provided to a dentist or dental technician in the substantially flattened and pre-looped configuration of FIGS. 2 and 4. In use, as shown in the FIGS. 5-6, the sensor holder is first opened into a loop away from the adjustable bond. Typically the sensor will have previously been placed into a sterile sleeve. The sensor and sleeve may then be inserted into the loop over the perforated fold line 28 if the dental sensor holder includes a perforated fold line. The adjustable bond 22 may be centered on the sensor body as shown in FIG. 6. The operator may than firmly pinch across the adjustable bond joining the portions of the adjustable bond into a bitewing and simultaneously securing the sensor.

As described above, the dental sensor holder is fabricated in part from a longitudinally elastic material. Thus, when the bitewing tab is formed as shown on FIG. 6, the loop may be made to stretch slightly around the sensor thus gently but securely holding the sensor.

The dental sensor holder and sensor included therein may then be placed into a patient's mouth in the conventional manner, the patient may be asked to bite down on the bitewing tab portion of the holder and a dental image may be obtained. As described above, the relatively soft strip material which covers all portions of the adjustable bond, in conjunction with the doubled strip thickness at the permanent bond provides an extremely smooth and comfortable biting surface for the patient which will not irritate adjacent cheek or tongue tissue.

After an image is obtained, the technician may safely remove the sensor by separating the adjustable bond at the base of the bitewing. In this manner the sensor may be removed without pulling on the data cable or otherwise applying undesirable stress to the delectate sensor apparatus.

As described above, a particular size of dental sensor holder 10 may accommodate various sensors having slightly different circumferences through the elasticity of the strip material and the ability to selectively engage some or the entire adjustable bond. The dental sensor holder may be provided in various sizes however, which correspond to categories of sizes of standardized digital sensor or phosphor x-ray plates.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments have been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A dental sensor holder comprising:
   a strip of material having a length, a width and two ends;
   a permanent bond joining the two ends to form a loop; and
   an adjustable bond joining adjacent portions of the strip extending from the permanent bond toward an opposite portion of the loop.

2. The dental sensor holder of claim 1 further comprising a fold line transverse the width of the strip away from the permanent bond.

3. The dental sensor holder of claim 1 wherein the adjustable bond comprises a hook and hook or hook and loop type fastener.

4. The dental sensor holder of claim 1 wherein the adjustable bond comprises:
   a first attachment surface operatively associated with the strip at an inner surface of the loop substantially adjacent to the permanent bond; and
   a second attachment surface operatively associated with the strip at an inner surface of the loop opposite from the first attachment surface and substantially adjacent to the permanent bond.

5. The dental sensor holder of claim 1 wherein the adjustable bond defines a biting surface.

6. The dental sensor holder of claim 5 wherein the permanent bond and the adjustable bond define a biting surface.

7. A method of fabricating a dental sensor holder comprising:
   providing a strip of material having a length, a width and two ends;
   associating first and second attachment surfaces with the strip; and
   permanently bonding the ends of the strip together to form a loop; wherein the first and second attachment surfaces may selectively be adjustably attached to each other.

8. The method of claim 7 further comprising providing a fold line transverse the strip between the first and second attachment surfaces.

9. The method of claim 7 further comprising providing an adjustable bond comprising a hook and hook or hook and loop type fastener.

10. The method of claim 7 further comprising providing an adjustable bond comprising:
    a first attachment surface operatively associated with the strip at an inner surface of the loop substantially adjacent to the permanent bond; and
    a second attachment surface operatively associated with the strip at an inner surface of the loop opposite from the first attachment surface and substantially adjacent to the permanent bond.

11. The method of claim 7 wherein the adjustable bond defines a biting surface.

12. The method of claim 11 wherein the permanent bond and the adjustable bond define a biting surface.

13. A method of supporting a dental sensor comprising:
    providing a dental sensor holder comprising:
      a strip of material having a length, a width and two ends;
      a permanent bond joining the two ends to form a loop; and
      an adjustable bond which can be selectively engaged to join adjacent portions of the strip extending from the permanent bond toward an opposite portion of the loop;
    placing a dental sensor into the loop; and
    engaging the adjustable bond causing the strip to support the sensor.

14. The method of claim 13 further comprising providing a dental sensor holder comprising a fold line transverse the strip between the first and second attachment surfaces.

15. The method of claim 13 further comprising providing a dental sensor holder comprising an adjustable bond comprising a hook and hook or hook and loop type fastener.

16. The method of claim 13 further comprising providing a dental sensor holder comprising an adjustable bond comprising:
    a first attachment surface operatively associated with the strip at an inner surface of the loop substantially adjacent to the permanent bond; and
    a second attachment surface operatively associated with the strip at an inner surface of the loop opposite from the first attachment surface and substantially adjacent to the permanent bond.

17. The method of claim 13 wherein the adjustable bond defines a biting surface.

18. The method of claim 17 wherein the permanent bond and the adjustable bond define a biting surface.

* * * * *